(12) United States Patent
Nishioka et al.

(10) Patent No.: US 6,213,936 B1
(45) Date of Patent: *Apr. 10, 2001

(54) BLADDER CONTROL DEVICE ACTUATOR

(75) Inventors: Craig Nishioka; Chi-Hong Shen, both of San Antonio, TX (US)

(73) Assignee: HK Medical Technologies Incorporated, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/196,842

(22) Filed: Nov. 20, 1998

(51) Int. Cl.$^7$ ........................................................ A61F 2/00
(52) U.S. Cl. ................................................................ 600/29
(58) Field of Search ................... 600/29–31; 128/DIG. 25

(56) References Cited

U.S. PATENT DOCUMENTS

| | | | |
|---|---|---|---|
| 3,642,004 | 2/1972 | Osthagen et al. | 128/349 R |
| 4,969,474 | 11/1990 | Schwarz | 128/885 |
| 5,078,676 | 1/1992 | Bailly | 600/31 |
| 5,090,424 | 2/1992 | Simon et al. | 128/885 |
| 5,114,398 | 5/1992 | Trick et al. | 600/29 |
| 5,131,906 | 7/1992 | Chen | 600/29 |
| 5,366,506 | * 11/1994 | Davis | 600/29 |
| 5,437,604 | 8/1995 | Kulisz et al. | 600/30 |
| 5,479,945 | 1/1996 | Simon | 128/885 |
| 5,509,888 | 4/1996 | Miller | 600/29 |
| 5,624,374 | * 4/1997 | Von Derestein | 600/29 |
| 5,701,916 | 12/1997 | Kulisz et al. | 128/885 |
| 5,704,353 | 1/1998 | Kalb et al. | 128/634 |
| 5,707,357 | 1/1998 | Mikhail et al. | 604/96 |
| 5,713,829 | 2/1998 | Hakky et al. | 600/29 |
| 5,722,932 | 3/1998 | Kulisz et al. | 600/29 |
| 5,795,288 | 8/1998 | Cohen et al. | 600/29 |
| 5,800,339 | 9/1998 | Salama | 600/29 |

* cited by examiner

Primary Examiner—John P. Lacyk
(74) Attorney, Agent, or Firm—Crompton, Seager & Tufte, LLC

(57) ABSTRACT

A system for initiating urine flow in intraurethral bladder control devices having a housing, a flow lumen, a valve biased to close, a distal end disposed near the urethral meatus, and a proximal end disposed near the bladder. The system includes an actuator device to open the valve. One intraurethral bladder control device has a higher velocity flow region near the valve distal end, such that the Bernoulli effect generates a negative pressure on the valve, keeping the valve in an open position once urine flow commences. One valve includes a spring biased stopper in the urine flow lumen. One actuator device is a suction device adapted to mate to the intraurethral device distal end and capable of pulling the stopper into the open position. Suction devices include plungers, syringes, and squeezable bulbs. Another actuator device includes a magnet capable of moving a magnetically responsive stopper. Yet another actuator device includes an elongate member disposed within the device housing and operably coupled to the stopper. Grasping and manipulating a free distal end of the elongate member causes the stopper to open and initiate urine flow.

22 Claims, 6 Drawing Sheets

BLADDER CONTROL DEVICE ACTUATOR

FIELD OF THE INVENTION

The present invention relates generally to medical devices and more particularly to intraurethral bladder control devices. Specifically, the invention relates to devices adapted to initiate urine flow in intraurethral devices and, more specifically, capable of initiating urine flow in users unable to generate sufficient bladder pressure due to atonic bladder disorder.

BACKGROUND OF THE INVENTION

The use of sphincter and bladder control devices is wide spread in the field of the present invention. See, for example, commonly assigned U.S. Pat. Nos. 5,512,032; 5,701,916; 5,701,916; and 5,722,932, herein incorporated by reference. Many existing intraurethral devices seek to duplicate the function of normal urinary sphincter control. This usually involves opening a valve in response to a user initiated stimulus, for example, an initial moment of high bladder pressure generated by the user of the device. In some devices, once begun, flow can be maintained without requiring continuing high bladder pressure.

There exists a class of potential users of these devices that cannot generate even a moment of sufficiently high bladder pressure to initiate flow through the aforementioned devices. Some users cannot generate pressure due to atonic bladder disorder. These individuals could maintain urination through some of the intraurethral devices, if the device could be initially opened to flow without requiring high bladder pressure. What has not been provided are devices and methods for initiating urine flow in devices in cases where the users can maintain flow through the devices, but cannot initiate urine flow.

SUMMARY OF THE PRESENT INVENTION

Devices and methods according to the present invention give a large number of people, previously unable to use intraurethral devices, the ability to deal with urinary incontinence using such devices. In particular, the present invention allows users of a class of intraurethral devices to initiate urine flow through the devices without having to generate high bladder pressure. One class of intraurethral devices within the scope of the present invention includes a substantially cylindrical housing having a wall, a proximal end having a proximal retainer, a distal end having a distal retainer, a valve therein, and a lumen therethrough. The proximal retainer is adapted to fit against the bladder wall and the distal retainer is adapted to fit against the urethral meatus.

The valve in a preferred device includes a stopper slidably disposed within the housing lumen and biased in a proximal direction so as to normally preclude urine flow. The stopper can typically rest proximally and tightly against a valve seat when closed and distally on standoffs against a retaining ring when open, leaving channels around the stopper for fluid flow. Once initiated, flow through the channels is of sufficiently high velocity so as to create a negative pressure on the stopper through the Bernoulli effect. In users not having significant bladder pressure problems, the user can initiate flow by forcing the stopper into a distal, open position with an initial moment of high bladder pressure. In users having significant problems, other methods and actuating devices according to the present invention can be used.

One system according to the present invention includes an intraurethral device as described above and a suction actuating device. One suction device includes a plunger having an end adapted to fit snuggly within the intraurethral device lumen, such that inserting the plunger within the lumen and rapidly withdrawing it generates a vacuum, causing the stopper to be pulled distally into the open position. Another suction device includes a syringe having an orifice adapted to mate to the intraurethral device lumen, such that forcing the syringe orifice against the intraurethral distal end and retracting the syringe plunger creates a negative pressure, thereby moving the stopper into the open position. Yet another suction device includes a squeezable bulb having an orifice adapted to mate to the intraurethral device distal end. The bulb can be squeezed or collapsed, the orifice can be forced against the intraurethral device distal end, and the bulb released, thereby generating suction and pulling the stopper into an open position.

One system according to the present invention includes an intraurethral device similar to that described above, but having a magnetically responsive stopper. A magnet can be included in the actuating device, such that the magnet can be used to force the stopper into the open position. In one system, the magnet is used to pull the stopper distally to open the valve.

In another system according to the present invention, an elongate member is disposed within the intraurethral device housing and coupled to the stopper. In one intraurethral device, the elongate member includes a flexible string or tape region, such that pulling on the elongate member causes tension in the elongate member and operates to force the stopper into the open position. In another intraurethral device, the elongate member includes a rod member capable of transmitting a compression force.

In use, the actuating device can be brought within an effective range of the intraurethral device and operated to force the stopper into the open position and allow urine flow to commence. Once urine is flowing within the device, high velocity flow through a channel of the valve generates a negative pressure through the Bernoulli effect. The negative pressure acts on the stopper to keep the stopper in the open position. Once urine flow drops below a certain threshold or stops altogether, the stopper, being biased to remain in the closed position, closes.

BRIEF DESCRIPTION OF THE PREFERRED EMBODIMENTS

DETAILED DESCRIPTION OF THE PREFERRED EMBODIMENTS

Figure 1:
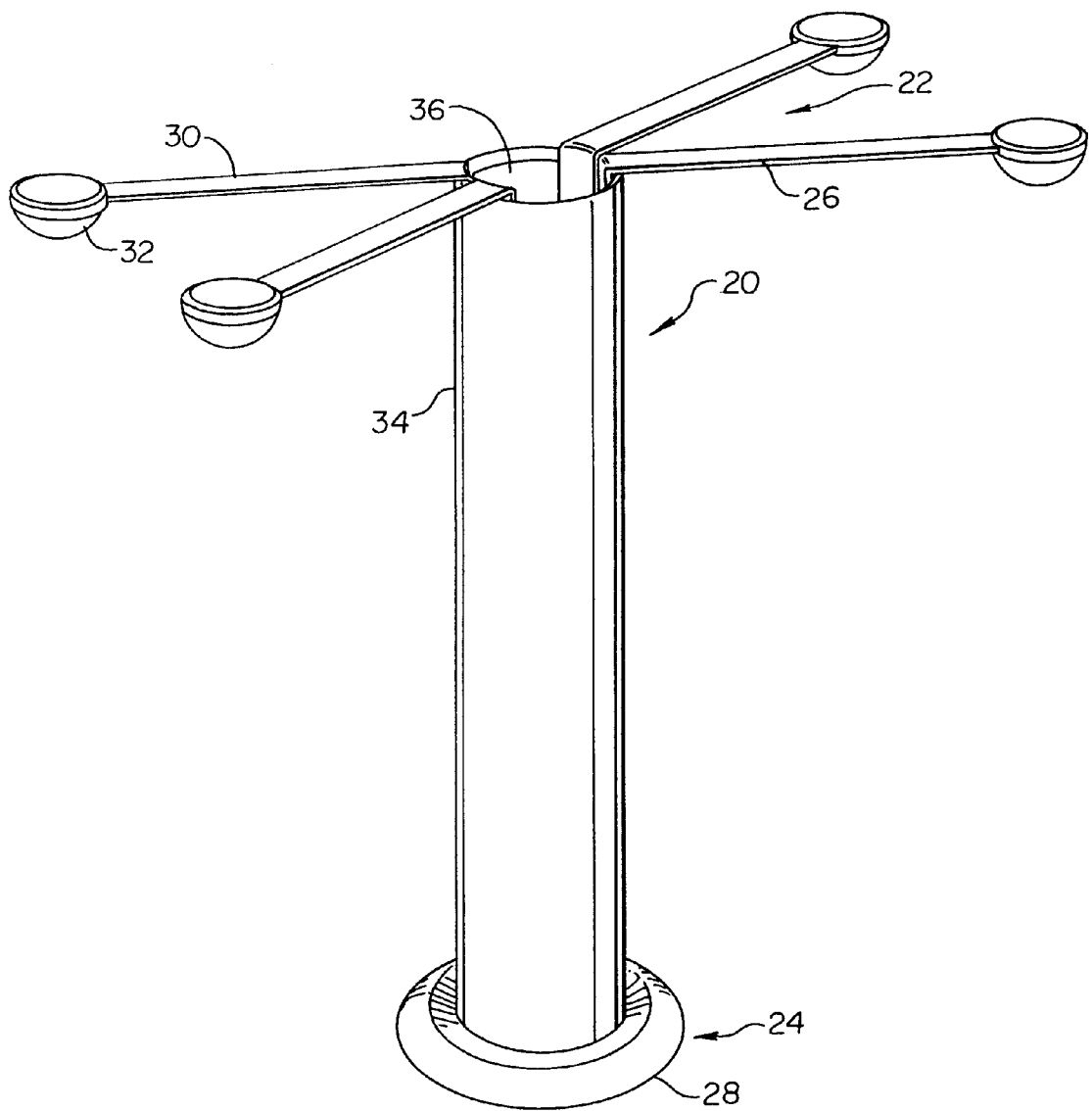
FIG. 1 is a perspective view of a bladder control device for insertion in a female urethra.
Figure 2:
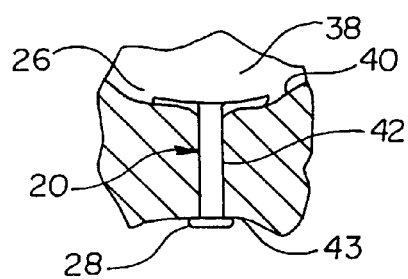
FIG. 2 is cutaway, fragmentary side view of the bladder control device of FIG. 1 disposed in a female urethra, between the bladder and urethral meatus.

FIG. 1 illustrates a bladder control device 20 having a proximal end 22 and a distal end 24, extending from a proximal retainer 26 through a housing 34 to a distal retainer 28. Proximal retainer 26 can include a plurality of leafs springs 30, preferably terminating in hemispheric safety pads 32. Housing 34 includes a urine lumen 36 extending therethrough, and a valve within. FIG. 2 illustrates bladder control device 20 disposed within a female bladder 38 and a urethra 42, extending between a bladder wall 40 and urethral meatus 43. Proximal retainer 26 prevents bladder control device 20 from migrating out of the body, while distal retainer 28 prevents migration into the body.

Figure 3:
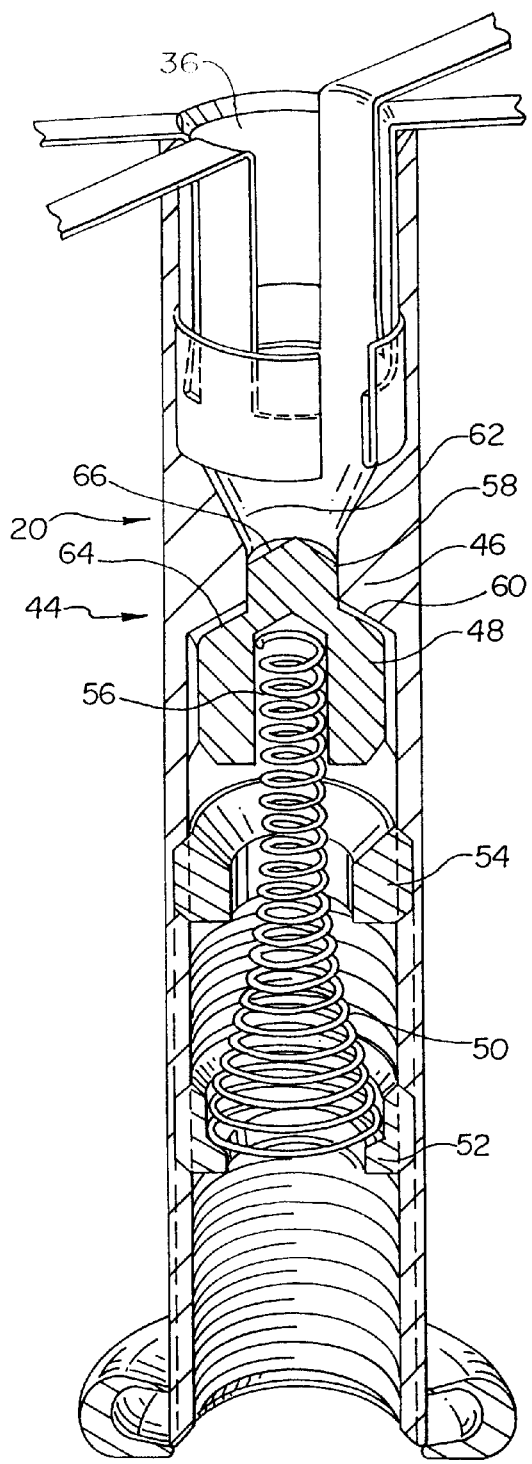
FIG. 3 is a cutaway, perspective view of the bladder control device of FIG. 1 having a urine flow lumen and a valve stopper in a proximal, closed position.

Referring now to FIG. 3, bladder control device 20 is illustrated in greater detail, showing a flow control valve 44 in a closed position. Valve 44 including a valve seat 46, a stopper 48, and a spring 50. In the embodiment shown, spring 50 biases stopper 48 against valve seat 46, thereby closing valve 44 and precluding urine flow through lumen 36. A spring mounting ring 52 retains spring 50 distally and a blind lumen 56 within stopper 48 bounds spring 50 proximally. A stopper retaining ring 54 limits the stopper distal travel and provides flow channels for urine between stopper 48 and stopper retaining ring 54. Valve seat 46 has a narrowing shoulder portion 58 and a narrower, constricted portion 60, leading to a lumen throat region 62. Stopper 48 has a stopper shoulder region 64 and a stopper proximal nose region 66. In the embodiment shown, in the closed position, stopper nose 66 fits snuggly within valve seat constricted region 60 and stopper shoulder 64 presses against valve seat shoulder 60.

Figure 4:
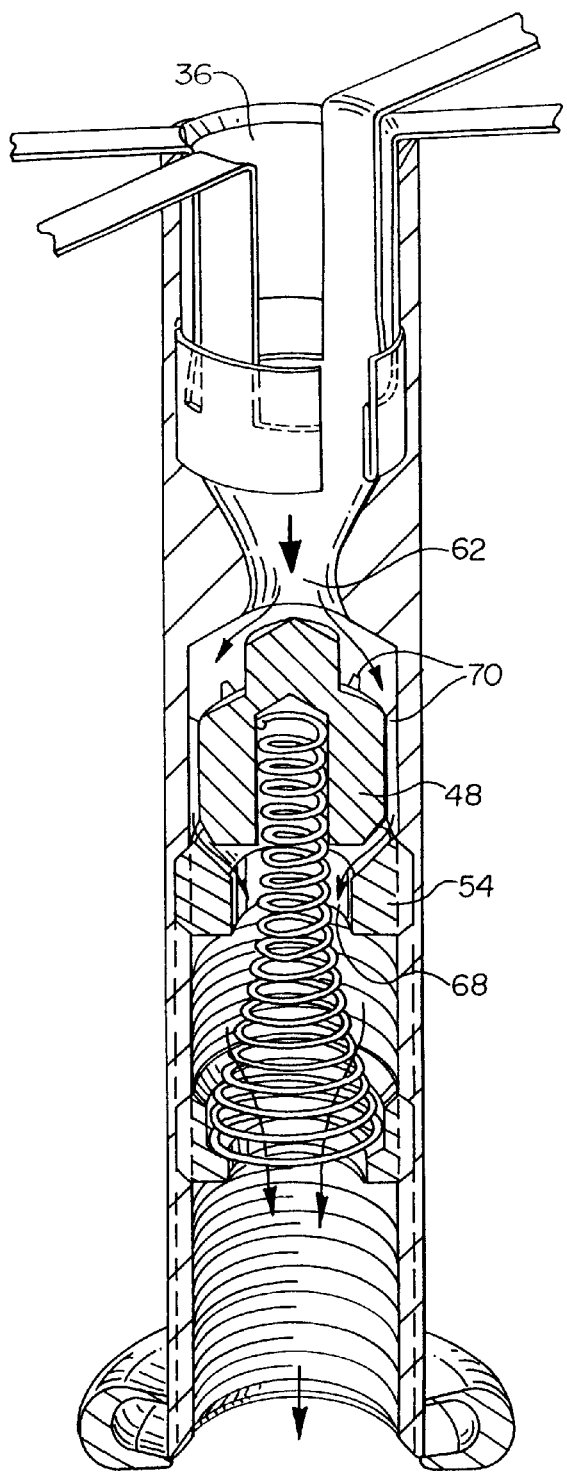
FIG. 4 is a cutaway, perspective view of the bladder control device of FIG. 3 having the valve stopper in a distal, open position.

Referring now to FIG. 4, bladder control device 20 is shown having valve 44 in open position, with stopper 48 near stopper retaining ring 54. Urine in flows through a channel 68 between stopper 48 and retaining ring 54. Standoffs 70 may be seen keeping stopper 48 nominally centered, away from the walls of housing 34, and away from retaining ring 54 allowing flow around the stopper, between the standoffs. As the cross sectional area available for flow is less than the area of throat 62, the fluid velocity is greater in channels 68 than in throat 62. The higher speed flow creates a negative pressure on stopper 48 through operation of the Bernoulli effect, acting to pull stopper 48 proximally, keeping valve 44 open. While open, valve stopper 48 has both nose 66 and shoulder 64 exposed to hydrostatic pressure. The greater amount of surface area exposed while open also serves to keep valve stopper 48 in open position.

In device users able to generate sufficient bladder pressure, an initial amount of bladder pressure is applied, bringing fluid pressure to bear on stopper 48, forcing stopper 48 proximally against spring 52 and moving the stopper axially downward to rest on retaining ring 54. The higher flow rate around stopper 48 between standoffs 70 and in channels 68 creates sufficient negative pressure on stopper 48 to hold valve 44 in the open position, even without any user applied bladder pressure. When the flow stops or decreases below a threshold, the negative pressure is no longer sufficient to oppose spring 50 and spring 50 forces stopper 48 to the closed position. Thus, while high bladder pressure is required to initially open valve 44, normal flow is sufficient to hold valve 44 open.

Figure 5:
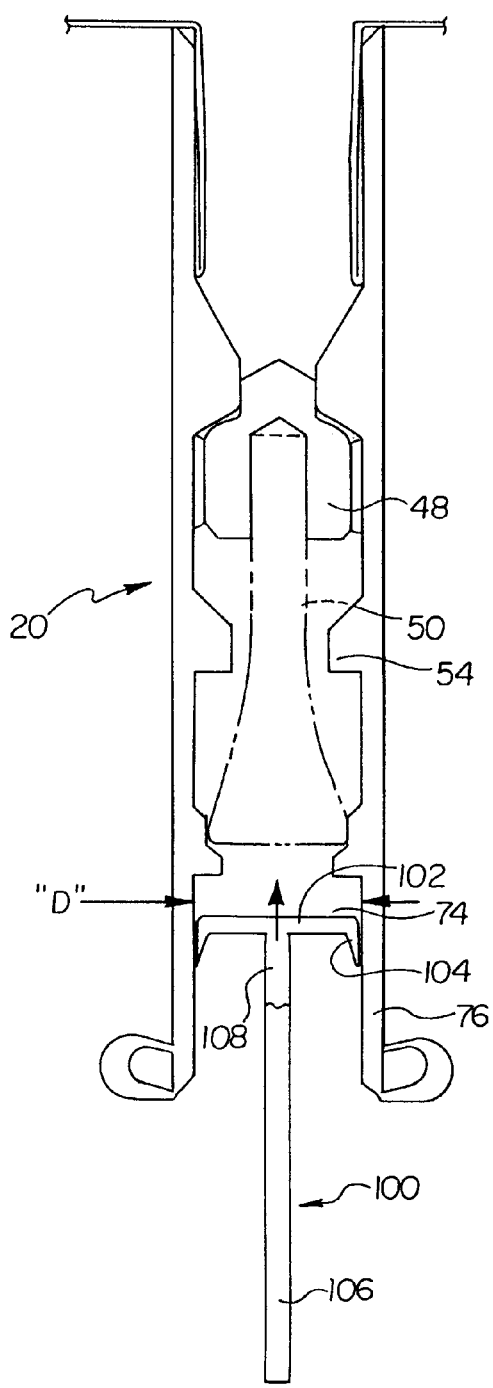
FIG. 5 is a cutaway, side view of the device of FIG. 1 in closed position, having a plunger actuator in the process of being positioned in the flow lumen.

In device users having an atonic bladder disorder, it may not be possible to generate bladder pressure sufficient to open valve 44. Referring now to FIG. 5, bladder control device 20 is again illustrated. Device 20 includes a distal lumen region 74 having housing wall 76 and an inside diameter indicated by "D". An actuator device in the form of a plunger 100 is inserted within distal lumen region 74, fitting snuggly against wall 76. In the embodiment shown, plunger 100 includes a head 102 having resilient outer edges 104. Attached to head 102 is an elongate central member 106 secured to plunger head 102. Elongate member 106 has a proximal portion 108. In one embodiment, elongate member 106 is a rigid, capable of pushing plunger head into lumen 74. In another embodiment, elongate member 106 is a flexible string or tape, secured to proximal portion 108 which is preferably rigid. In this tape embodiment, a finger or other member can be used to insert plunger head 102 within lumen region 74.

Figure 6:
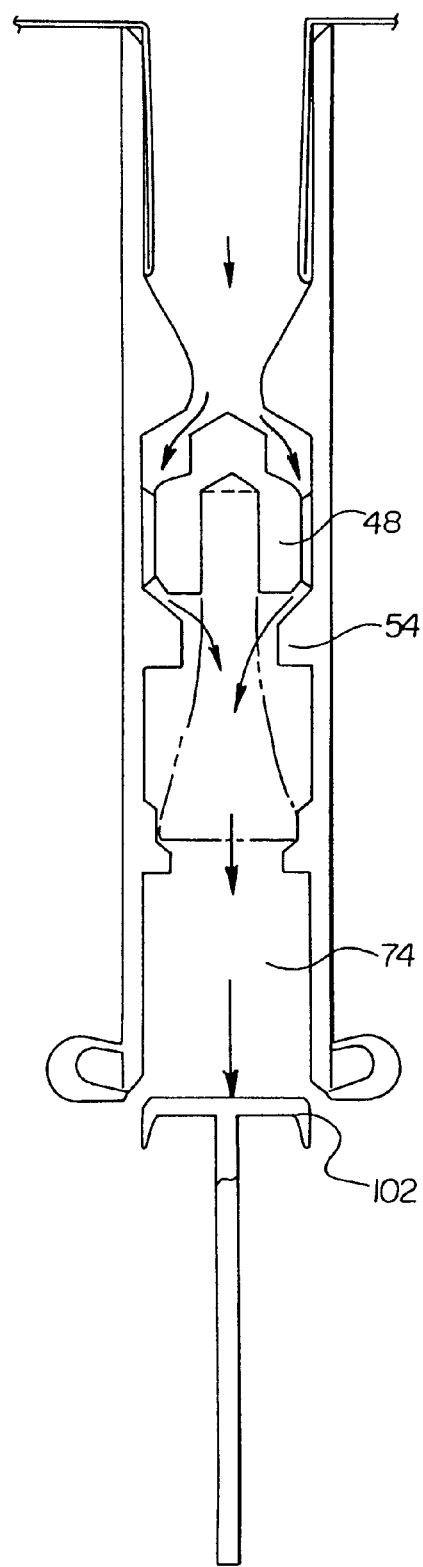
FIG. 6 is a cutaway, side view of the device of FIG. 6 in open position, after the plunger has been withdrawn and urine flow initiated.

After insertion, when urine voiding is desired, elongate member 106 can be grasped and pulled in a distal direction, away from bladder control device 20. This action is illustrated in FIG. 6. This action causes plunger head 102 to slide out of lumen region 74, creating a suction or negative pressure. This suction causes stopper 48 to move axially and distally toward retaining ring 54, allowing urine to flow past stopper 48, thereby initiating the Bernoulli effect and the resultant negative pressure. The flow caused negative pressure should then be sufficient to maintain stopper 48 in open position until urine flow decreases below a threshold or stops. After urine voiding is complete, the previous plunger or a fresh plunger can be inserted.

Figure 7A:
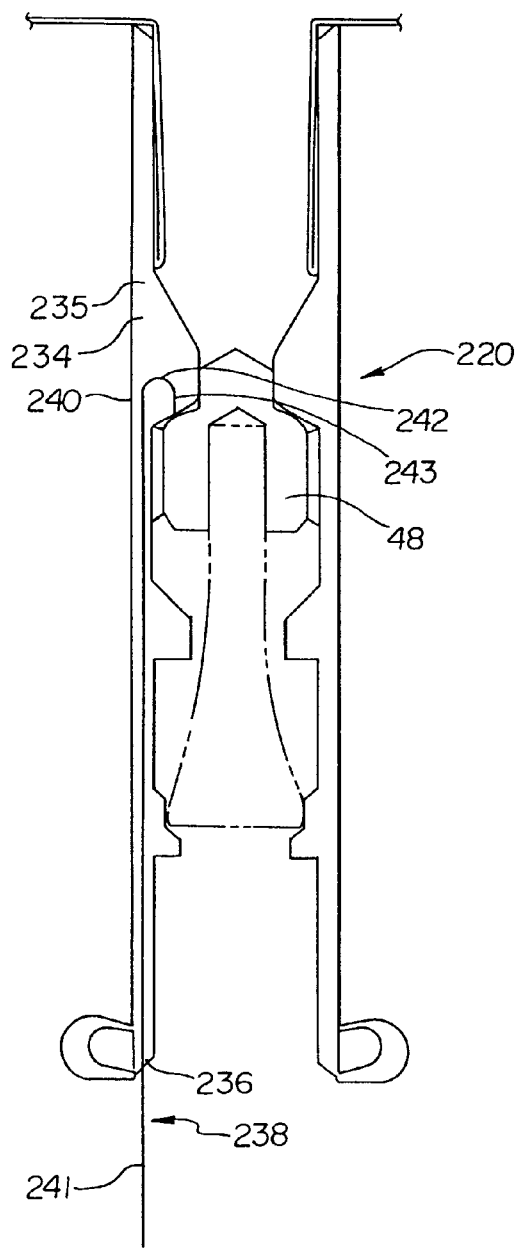
FIG. 7A is a cutaway, side view of a bladder control device in closed position having a housing wall including a lumen therein, and an elongate actuating member disposed within the wall lumen.

Referring now to FIG. 7A, another embodiment is illustrated in a bladder control device 220. Device 220 includes a housing 234, a housing wall 235, and a lumen 236 disposed within housing wall 235. An actuator device in the form of an elongate member 238 is slidably disposed within lumen 236. Elongate member 238 includes a distal portion 241 and a proximal portion 240. Proximal portion 240 includes an arcuate, U-shaped portion 242 which includes a tip 243 which can be brought to bear on stopper 48. In one embodiment, elongate member 238 is formed of a rigid material capable of bearing tension and compression forces without significant buckling. In another embodiment, U-shaped portion 242 can bear compression force while distal portion 241 is a string or tape which can transmit only tension force.

Figure 7B:
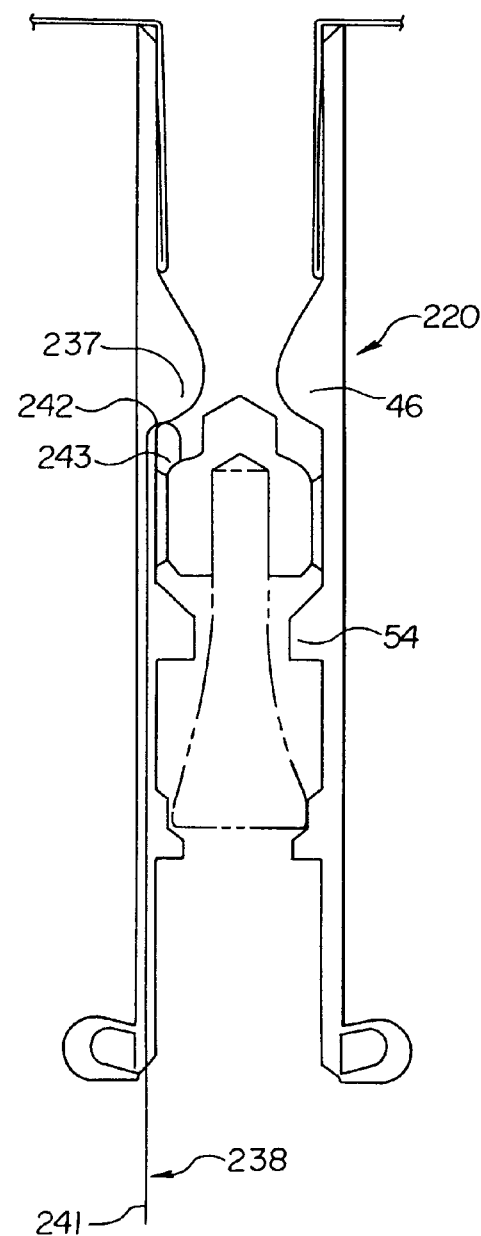
FIG. 7B is a cutaway, side view of the bladder control device of FIG. 7A, having the elongate member distally moved, causing the valve stopper to open.

Referring now to FIG. 7B, use of bladder control device 220 and actuator elongate member 238 is illustrated. When urine voiding is desired, the externally accessible portion of member distal portion 241 can be grasped by the wearer and pulled away from device 220. In one embodiment, lumen 236 includes a proximal, wide, slotted region 237, allowing arcuate portion 242 some travel in a proximal-distal direction. Arcuate portion 242 is thereby pulled distally, brining tip 243 to bear on stopper 48, thereby forcing stopper 48 away from valve seat 46 and toward retaining ring 54, thereby opening the valve and initiating urine flow. Once urine flow commences, the forces previously discussed serve to keep stopper 48 in the open position until flow sufficiently decreases or stops. The coupling force between the grasped member and stopper 48 thus includes both tension and compression in the embodiment illustrated in FIG. 7B.

Figure 8A:
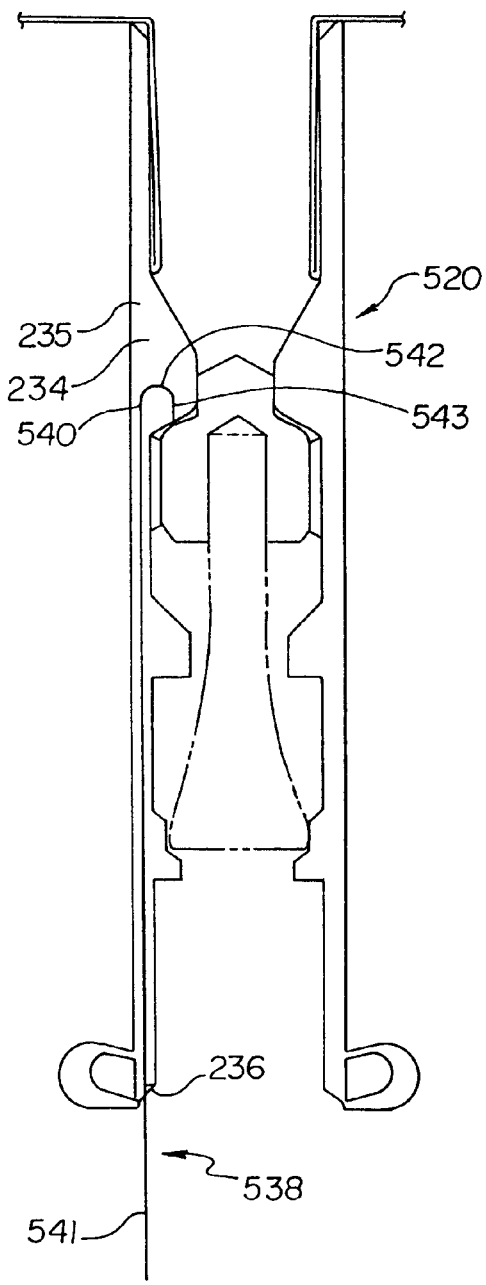
FIG. 8A is a cutaway, side view of a bladder control device in a closed position having a housing wall including a lumen therein, and an elongate member disposed within the wall lumen.

Referring now to FIG. 8A, another embodiment is illustrated in a bladder control device 520. Device 520 includes housing 234, housing wall 235, and lumen 236 disposed within housing wall 235. An actuator device in the form of a pushable elongate member 538 is slidably disposed within lumen 236. Elongate member 538 includes a distal portion 541 and a proximal portion 540. Proximal portion 540 includes an arcuate, U-shaped portion 542 which includes a tip 543 which can be brought to bear on stopper 48. In one embodiment, elongate member 538 is formed of a rigid material capable of bearing compressive forces without significant buckling. In particular, the portion of elongate member 538 near tip 543 should be capable of bearing compressive forces without buckling.

Figure 8B:
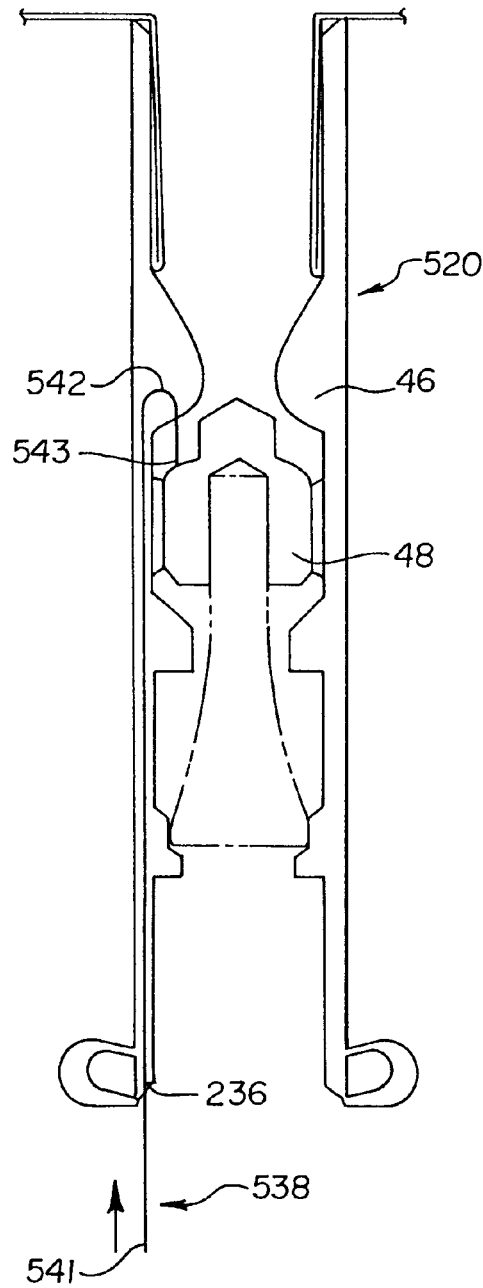
FIG. 8B is a cutaway, side view of the bladder control device of FIG. 8A, having the elongate member proximally pushed, causing the valve stopper to open.

Referring now to FIG. 8B, use of bladder control device 520 and elongate actuator member 538 is illustrated. When urine voiding is desired, the externally accessible portion of member distal portion 541 can be grasped by the user and pushed into device 520. Arcuate portion 542 is thereby subject to compression, forcing member 538 to slide through lumen 236 and forcing tip 543 to bear on topper 48, thereby forcing stopper 48 away from valve seat 46. In this embodiment, over most of its length, elongate member 538 is supported against buckling by lumen 236.

Figure 9:
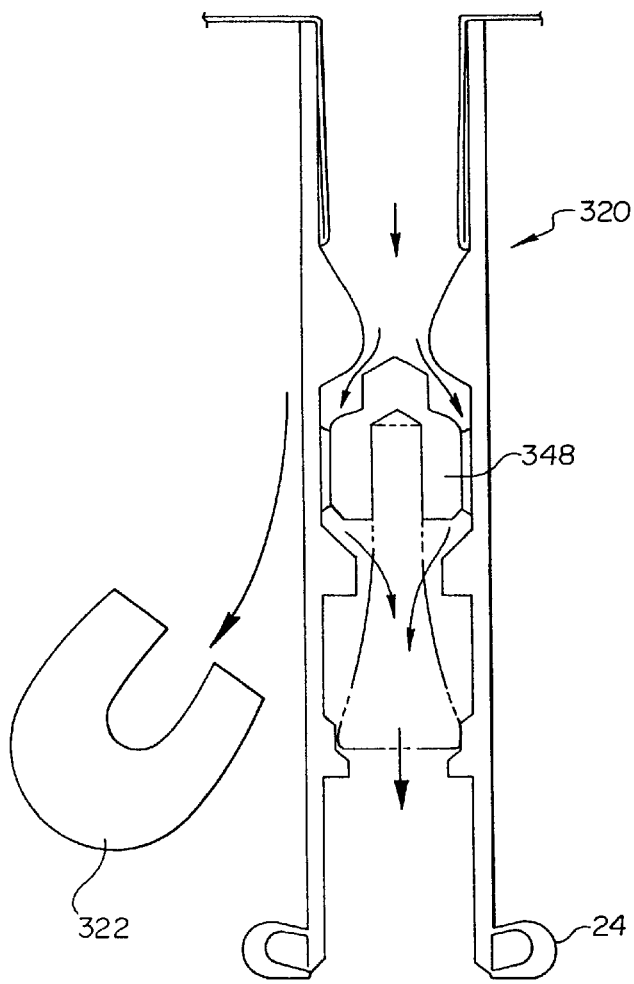
FIG. 9 is a cutaway, side view of a bladder control device having a magnetically responsive valve stopper and an actuator magnet capable of forcing the stopper into an open position.

Referring now to FIG. 9, another bladder control device 320 is illustrated. Device 320 uses a magnet 322 as an actuator and magnetic force as a coupling force. In device 320, a magnetically responsive stopper 348 is included in the device. As used herein, "magnetically responsive" means capable of being attracted or repelled by a magnetic force. In one embodiment, stopper 348 if formed of a magnetically responsive material. In one embodiment, a magnetically responsive material is enclosed in a protective, polymeric layer. In another embodiment, a magnetically responsive material is embedded in a polymeric material. In yet another embodiment, a magnetic member is operably secured to the stopper. One class of magnetic materials suitable for use in a magnetic embodiment includes ferromagnetic materials.

In use, magnetic actuator 322 can be brought within its effective range, sufficiently close to exert an attractive force on stopper 348. Magnet 322 can then be moved alongside or "swiped" over device 320, substantially parallel to the longitudinal axis. The magnetic force acting on the stopper pulls the stopper away from valve seat 46 and toward retaining ring 54. In another method, magnet 322 is disposed near distal end 24, with the magnet having sufficient effective range to pull stopper 348 into an open position. After flow has been initiated, magnet 322 can be removed, and urine flow continues.

Figure 10:
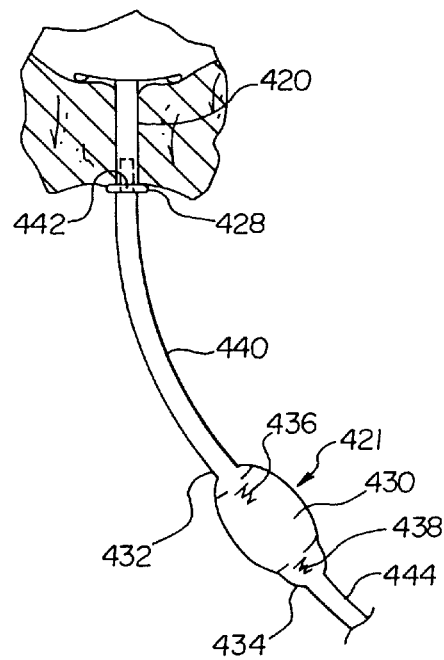
FIG. 10 is a cutaway, side view of a bladder control device inserted into a female urethra, having a suction device orifice mated to the flow control device distal end.

Referring now to FIG. 10, another bladder control device 420 is illustrated. Device 420 includes a distal end 428 in fluid communication with a urine flow lumen. An actuator in the form of a suction device 421 is illustrated, having a squeezable bulb 430 in communication with an inlet tube 440 and, preferably, an outlet tube 444. The coupling force between bulb 430 and the bladder device is a negative pressure or suction. Inlet tube 440 has an orifice 442 adapted to mate to bladder device distal end 428. Suction bulb 430 has an inlet end 432 and an outlet end 434. Inlet end 432 has a one way valve 436, and outlet end 434 also has a one way valve 438. Inlet one way valve 436 allows fluid into the bulb and outlet valve 438 allows fluid out of the bulb into outlet tube 444.

In use, inlet tube 440 can be mated to device distal end 428. Bulb 430 can be squeezed, partially collapsing the bulb and forcing air out through outlet valve 438 while inlet valve 436 remains shut. When released, bulb 430 expands, outlet valve 438 is pulled shut by the vacuum, directing the vacuum through now open inlet valve 436. Once urine flow is initiated, the urine can flow through bulb 430 and outlet valve 438, through outlet tube 444. In one embodiment, outlet valve 438 closes in the presence of vacuum in bulb 430, but remains open in the absence of suction pressure. Outlet tube 444 can lead to a reservoir for holding urine. Suction device 421 is suitable for use in institutions in general, and for bed-ridden patients in particular.

Figure 11:
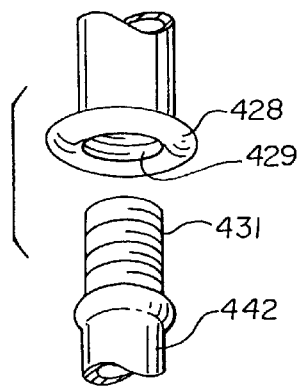
FIG. 11 is a fragmentary, perspective view of the distal end of a bladder control device and a suction device tube adapted to be inserted within the bladder control device lumen.
Figure 12:
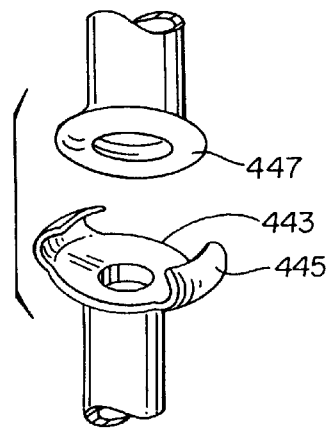
FIG. 12 is a fragmentary, perspective view of the distal end of a bladder control device and a suction device tube adapted to abut the flow control device distal end.

Referring now to FIG. 11, bladder control device distal end 428 is further illustrated, having an inlet 429 adapted to receive a tip 431 of tube 442 within. In one embodiment, tip 431 has a plurality of ribs to secure tip 431 within device end 428. Referring now to FIG. 12, another tip 443 is illustrated, having a pair of wings 445 for wrapping around a lip 447 on device distal end 428. Wings 445 are preferably formed of an elastomeric, resilient material adapted to receive lip 447. Tip 443 can be fit over lip 447 for the duration of the urine voiding and subsequently removed.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A system for providing female urinary bladder flow control comprising:
   a housing including a lumen, said housing adapted to fit in a female urethra;
   a valve in fluid communication with said lumen having an open position permitting flow from said bladder and a closed position obstructing flow from said bladder, said valve being biased to remain in said closed position, said valve having a first region and a second region, said second region having a smaller flow channel and a higher fluid velocity therethrough than said first region, such that a Bernoulli effect induced negative pressure acts to keep said valve in said open position when fluid is flowing through said second region; and
   an actuator adapted to force said valve into said open position, the actuator having a portion extending from the housing and the female urethra when the housing is placed within the female urethra.

2. A system as recited in claim 1, wherein said urethra has a meatus;
   said housing has a distal region for disposition near said urethral meatus, said lumen in said distal region having a distal inside diameter; and the portion of the actuator extending from the housing; including a plunger, said plunger including a portion having an outside diameter adapted to slide snuggly within said housing lumen distal inside diameter, such that withdrawing said plunger from said lumen causes a negative pressure to act upon and open said valve.

3. A system as recited in claim 1, wherein said urethra has a meatus;

said housing has a distal region for disposition near said urethral meatus; and the portion of the actuator extending from the housing includes a suction device adapted to mate to said lumen distal region, such that said suction device can be operated to cause a negative pressure to act upon and open said valve.

4. A system as recited in claim 3, wherein said suction device includes a squeezable bulb having an orifice adapted to mate to said lumen distal region.

5. A system as recited in claim 4, wherein said squeezable bulb includes an interior and an inlet tube, said inlet tube having a free end and a lumen in communication with said bulb interior, wherein said orifice is disposed at said free end.

6. A system as recited in claim 1, wherein said housing includes a longitudinal axis, wherein the portion of the actuator extending from the housing includes an elongate member disposed within said housing and having a distal region accessible from outside of said housing, said elongate member being operably coupled to said valve, such that sliding said elongate member causes said valve to assume said open position.

7. A system as recited in claim 6, wherein said elongate member includes a flexible portion, such that distally sliding said elongate member causes tension in said flexible portion and pulls said valve into said open position.

8. A method for controlling fluid flow in a bladder control device comprising the steps of:

providing a bladder control device for insertion in a female urethra including:
 a housing having a lumen therethrough; and
 a valve in fluid communication with said lumen, said valve having an open position permitting fluid flow from said bladder and a closed position obstructing fluid flow from said bladder, said valve having means for biasing said valve in said closed position and means responsive to fluid flow for remaining in said open position in response to said fluid flow;

providing actuating means for opening said valve the actuating means having a portion extending from the housing and the female urethra when the housing is placed in the female urethra;

providing means for coupling said actuating means to said valve, said coupling means having an effective range, such that force applied to said actuating means is coupled to said valve, such that applying force to said actuating means causes said valve to assume said open position, such that said biasing means closes said valve in the absence of fluid flow;

disposing said actuating means within said coupling means effective range;

applying force to said actuating means, such that said force is coupled to said valve and said valve is opened, permitting said fluid flow from said bladder; and closing said valve upon the cessation of fluid flow, said closing being accomplished through said valve biasing means.

9. A method as recited in claim 6, wherein said means responsive to fluid flow includes fluid pressure acting to hold said valve in said open position, said fluid pressure including pressure generated by the Bernoulli principle in response to said fluid flow.

10. A method as recited in claim 8, wherein said means responsive to fluid flow includes fluid pressure acting to hold said valve in said open position, wherein said valve has a first surface area exposed to fluid pressure from said bladder when said valve is in said closed position, and a second surface area exposed to fluid pressure from said bladder when said valve is in said open position, said second surface area being larger than said first area, such that said means responsive to fluid flow includes a greater force acting upon said valve to open said valve when said valve is in said open position than in said closed position.

11. A method as recited in claim 8, wherein said housing lumen has a distal portion having a distal inside diameter;

said actuating means includes a plunger having an outside diameter adapted to slide snuggly within said distal lumen portion;

said coupling means includes suction pressure between said plunger and said valve; and said force applying step includes withdrawing said plunger from said lumen, such that a suction pressure acts upon said valve, forcing said valve into said open position.

12. A method as recited in claim 8, wherein said housing lumen has a distal portion having a distal inside diameter;

said actuating means includes a suction device capable of creating a suction pressure and adapted to mate to said distal lumen portion;

said coupling means includes suction pressure between said suction device and said valve; and said force applying step includes creating a suction in said suction device, such that mating said suction device to said lumen and creating said suction pressure acts upon said valve to force said valve into said open position.

13. A method as recited in claim 12, wherein said suction device includes a squeezable bulb having an interior and an orifice in fluid communication with said interior, wherein said orifice is adapted to mate to said lumen distal portion.

14. A method as recited in claim 13, wherein said suction device includes a tube having a lumen in fluid communication with said bulb interior and having said orifice in fluid communication with said lumen.

15. A method as recited in claim 8, wherein said valve includes magnetically responsive material;

said actuating means includes a magnetic device having an effective range;

said coupling means includes magnetic force; and said force applying step includes bringing said magnetic device within said effective range and allowing said magnetic force to move and open said valve.

16. A method as recited in claim 8, wherein said valve includes magnetically responsive material;

said actuating means includes a magnetic device having an effective range;

said coupling means includes magnetic force; and said force applying step includes bringing said magnetic device within said effective range and moving said magnetic device, such that said moving force is magnetically coupled to said valve and said valve is opened.

17. A method as recited in claim 16, wherein said urethra is disposed below a pubic area;

said magnetic device is a permanent magnet; and said moving step includes moving said magnet along the surface of said pubic area.

18. A method as recited in claim 8, herein said valve includes magnetically responsive material;

said actuating means includes a magnetic device having an effective range;

said coupling means includes magnetic force; and said force applying step includes bringing said magnetic device within said effective range, such that said moving force is magnetically coupled to said valve and said valve is opened.

19. A method as recited in claim 18, wherein said coupled magnetic force is an attractive force.

20. A method as recited in claim 8, wherein said actuating means includes an elongate member having a proximal portion disposed within said bladder control device, said elongate member having a distal portion accessible from without said bladder control device, said elongate member being operably coupled to said valve;

said coupling means includes force brought to bear upon said valve by said elongate member; and said force applying step includes applying force to said elongate member, such that said valve is opened.

21. A method as recited in claim 20, wherein said coupling means includes a tension force and said force applying means includes pulling said elongate member away from said urethra.

22. A method as recited in claim 20, wherein said housing includes a wall having a lumen therein;

said coupling means includes an elongate member having said proximal portion disposed within said wall lumen; and said coupling means includes a compression force and said force applying step includes pushing said elongate member toward said urethra.

* * * * *